United States Patent [19]
Gillespie

[11] Patent Number: 5,180,370
[45] Date of Patent: Jan. 19, 1993

[54] SAFETY HYPODERMIC SYRINGE WITH RETRACTABLE NEEDLE

[76] Inventor: Elgene R. Gillespie, 353 Freedom Ave. NE., Canton, Ohio 44704

[21] Appl. No.: 884,389

[22] Filed: May 18, 1992

[51] Int. Cl.⁵ .............................................. A61M 5/00
[52] U.S. Cl. .................................... 604/110; 604/195
[58] Field of Search ............... 604/110, 187, 195, 218, 604/192, 263

[56] References Cited

U.S. PATENT DOCUMENTS

| | | | |
|---|---|---|---|
| 4,728,320 | 3/1988 | Chen | 604/110 |
| 4,838,863 | 6/1989 | Allard et al. | 604/110 |
| 4,915,699 | 4/1990 | Kornberg | 604/195 |
| 4,921,486 | 5/1990 | DeChellis et al. | 604/110 |
| 4,950,241 | 8/1990 | Ranford | 604/110 |
| 4,973,316 | 11/1990 | Dysarz | 604/110 |
| 4,978,343 | 12/1990 | Dysarz et al. | 604/110 |
| 5,000,736 | 3/1991 | Kaufhold, Jr. et al. | 604/110 |
| 5,000,738 | 3/1991 | LaVallo et al. | 604/110 |
| 5,019,044 | 5/1991 | Tsao | 604/110 |
| 5,024,616 | 6/1991 | Ogle, II | 604/110 |
| 5,049,133 | 9/1991 | Pascual | 604/110 |
| 5,053,010 | 10/1991 | McGary et al. | 604/110 |
| 5,064,419 | 11/1991 | Gaarde | 604/110 |

Primary Examiner—John D. Yasko
Attorney, Agent, or Firm—Paul E. Milliken; Lee A. Germain

[57] ABSTRACT

A syringe for giving medical injections which has an internal mechanism for retracting the needle into the syringe after the injection has been given and locking the needle and plunger inside the barrel of the syringe to reduce the risk of accidental needle pricks. In one embodiment the needle is manually retracted by pulling back on the plunger and in the other embodiment the needle is propelled by a compressed spring into a hollow chamber within the plunger.

29 Claims, 3 Drawing Sheets

SAFETY HYPODERMIC SYRINGE WITH RETRACTABLE NEEDLE

FIELD OF THE INVENTION

This invention relates generally to hypodermic syringes and in particular to the type having retractable needles which are withdrawn into the barrel and/or plunger after an injection has been given, thereby preventing accidental needle pricks which could transmit AIDS, hepatitis and other infectious diseases.

BACKGROUND OF THE INVENTION

In the past various attempts have been made to design hypodermic syringes with retractable needles. Typical examples of such devices are shown in U.S. Pat. Nos. 4,838,863; 5,019,044; 5,064,419; 4,950,241; and 4,978,343.

Some of these patents show the needle retracted into a hollow piston or barrel of a syringe either manually or by a spring which is biased to move the needle into a stored position either within a hollow piston or at least within the barrel of a hypodermic syringe. Such devices are only as effective and reliable as the design of the mechanisms used to retract the needle and some mechanisms may either fail to retract the needle completely or may fail to retain the needle in a retracted position.

OBJECTS OF THE INVENTION

It is a primary object of this invention to provide a hypodermic syringe with a retractable needle which is simple, reliable and which will securely retain the needle in the retracted position.

Another object of this invention is to provide a hypodermic syringe with retractable needle wherein the plunger or piston is securely locked in a depressed position within the barrel of the syringe after the needle is retracted into the plunger to prevent removal of the needle.

A still further object of this invention is to proved a hypodermic syringe with retractable needle which is inexpensive to manufacture and easy to use.

These and other objects of the invention will become more fully apparent in the following specification and the attached drawings.

SUMMARY OF THE INVENTION

This invention is a safety hypodermic syringe comprising a hollow barrel for containing a fluid, the barrel having a rear end opening and a front end opening, a hollow needle extending through the front end opening of the barrel to permit fluid from the barrel to be injected through the needle, a mounting means temporarily securing the needle within the front end of the barrel with the needle protruding forwardly from the front end opening of the barrel until an injection given by the needle has been completed, a hollow plunger containing an axial chamber therein which is large enough to receive the needle and mounting means therein, the plunger having a front end inserted through the rear end opening of the barrel and being slideable longitudinally within said barrel to move inwardly when pressure is applied to an outwardly extending rear end of the plunger, the front end of the plunger being open for communication between the axial chamber and the interior of the barrel except when the end is initially covered by an end cover which temporarily seals the chamber of the plunger until the plunger is depressed a sufficient distance to complete the injection of fluid from the chamber through the needle, means removing the end cover from the front end of the plunger, a means for moving the needle rearwardly out of the front end opening of the barrel with at least part of the mounting means and into a stored position within the hollow plunger, and a means to retain the needle and mounting means in the stored position to prevent the needle from protruding from the front end of the barrel.

DESCRIPTION OF THE PREFERRED EMBODIMENTS

Figure 1:
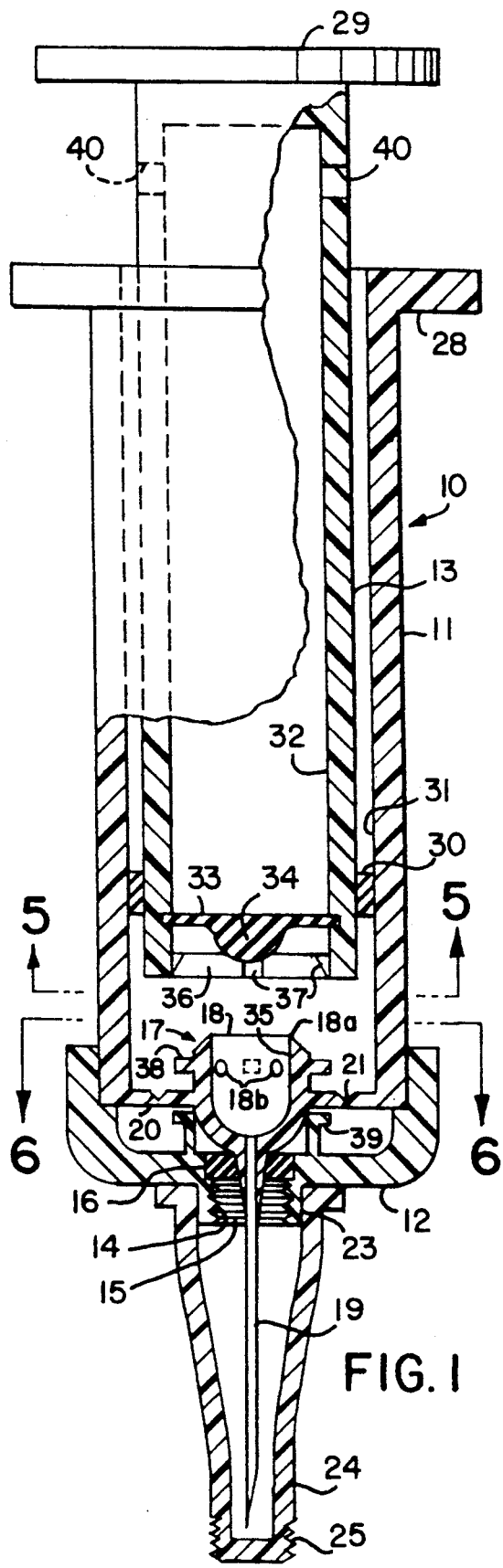
FIG. 1 is a side elevational view of a syringe illustrating one embodiment of the invention with portions broken away to show the internal mechanism of the invention.

Referring now to the drawings and in particular to FIG. 1 which shows a manually retractable needle embodiment, a hypodermic syringe is indicated generally by the numeral 10. The syringe 10 has a hollow cylindrical barrel 11 which is open at the rear end and covered at the front end by a front end cap 12 which is secured adhesively or by other suitable means to the barrel 11. The end cap 12 has a center hole 14, part of which has internal threads 15 and the remainder carries an elastomeric seal ring 16.

Figure 6:
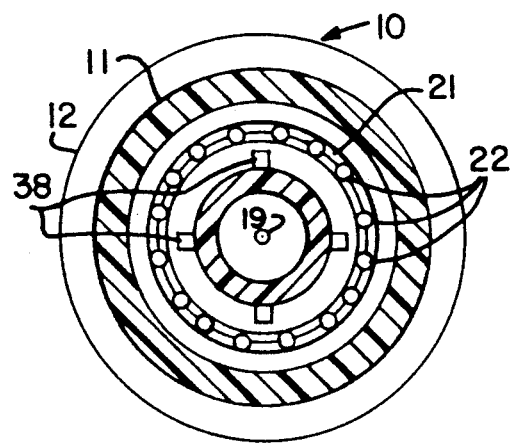
FIG. 6 is a cross-sectional view taken on line 6—6 of FIG. 1.
Figure 7:
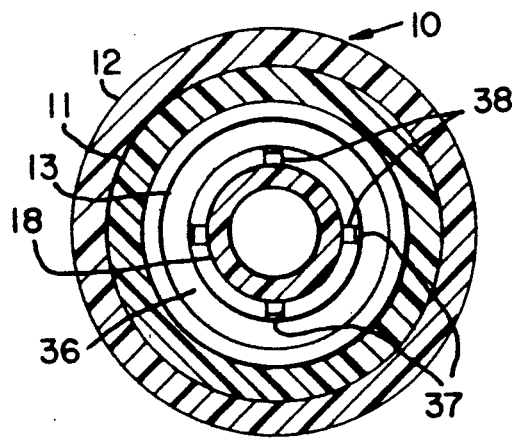
FIG. 7 is a cross-sectional view taken on line 7—7 of FIG. 2.

Attached to the front end of the barrel 11 is a needle assembly 17 which includes a head member 18 containing a needle 19 molded therein and a radially outwardly extending annular connector wall 20 extending between the barrel 11 and the needle head member 18 to temporarily secure the needle in the end of the barrel 11 with the needle 19 projecting out through the center hole 14 and sealing with the ring 16 to prevent fluid from leaking from the barrel 11 around the outside of the needle 19. The connector wall has an annular groove 21 to serve as a weakened portion to permit the needle head 18 to be broken away from the barrel 11 as will be explained later. The groove 21 may contain a plurality of holes 22 spaced apart around the groove 21, as shown in FIG. 6, to further weaken the area of the groove 21 to permit break-away of the needle head 18 as will be explained later.

The cap 12 has an outwardly projecting shoulder portion 23 in axial alignment with the center hole 14 for receiving a sheath 24 which covers the needle 19 until it is removed to give an injection. The sheath 24 has a break-away threaded plug 24 at the front end thereof which is screwed into the threaded portion of the center hole 14 to retain the needle 19 inside the barrel 11 after it has been retracted.

Figure 4:
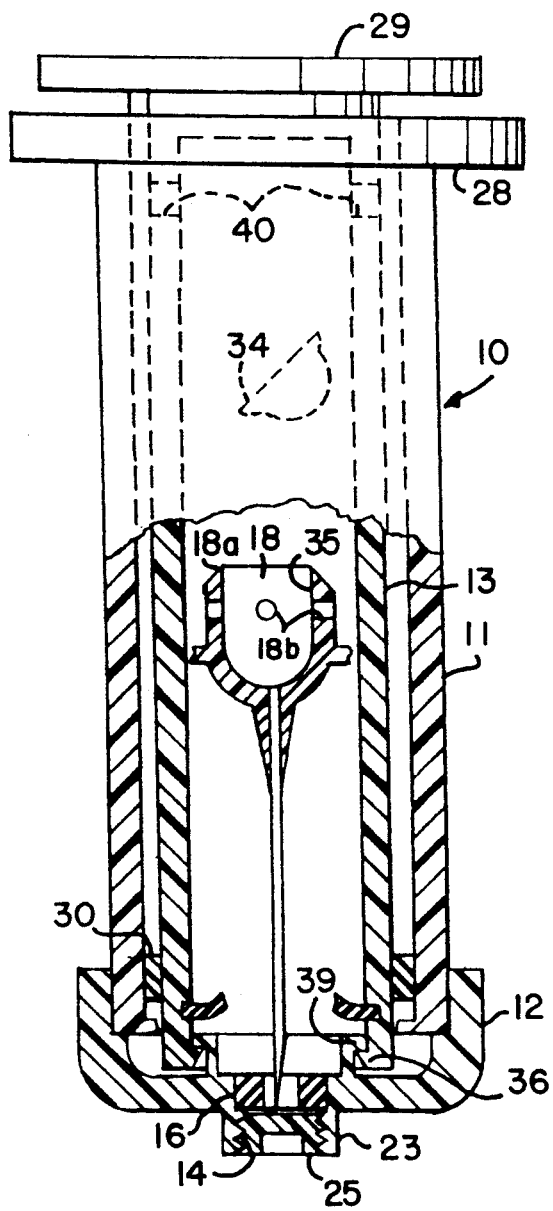
FIG. 4 is a fragmentary side elevational view of the syringe shown in FIG. 1 with portions broken away to shown the needle stored inside the hollow plunger and the plunger locked in the fully depressed position within the barrel.
Figure 4A:
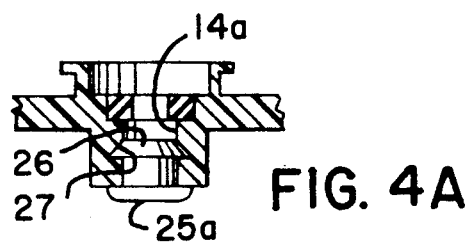
FIG. 4A is a fragmentary cross-sectional view showing an alternative closure plug to that shown in the front end of the barrel in FIG. 4.

Another modified type of plug 25a is shown in FIG. 4A wherein the plug snaps into the hole 25a instead of being screwed into position. A radially extending rib 26 on the plugs 25a engages a groove 27 in the hole 25a to retain the plug 25a in the hole.

The barrel 11 has a radially outwardly extending flange 28 at the rear end thereof to aid in holding the barrel 11 while depressing the plunger 13 by pressing on an enlarged end plate 29 on the rear end of the plunger 13.

The plunger 13 fits inside the barrel 11 and is moveable axially backward and forward within the barrel. An annular seal ring 30 surrounds the plunger 13 near the front end thereof and provides a seal with the inner wall surface 31 of the barrel 11 to retain injection fluid and pressure within the barrel 11. The plunger 13 has a hollow chamber 32 which is sealed from the interior of the barrel 11 by a resilient rupturable cover 33 made preferably of elastomeric material. The cover has a hemispherical portion 34 which extends forwardly to extend into a hollow cup shaped cavity 35 in the needle head 18 to aid in expelling fluid from the cavity when the plunger 13 is depressed.

Figure 5:
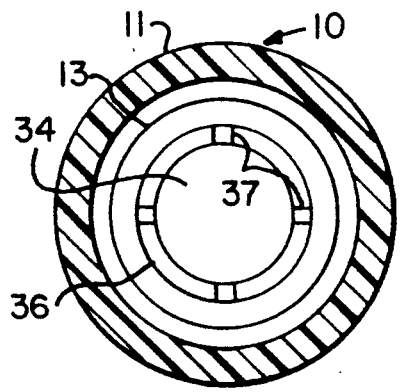
FIG. 5 is a cross-section view taken on line 5—5 of FIG. 1.

At the front end of the plunger 13, an annular rib or ledge 36 extends radially inwardly for performing a function to be described later. The rib 36 contains a plurality of spaced apart radially extending slots 37 also shown in FIG. 5 for engaging radially outwardly extending pegs 38 on the needle head 18. When the slots 37 engage the pegs 38, rotation of the plunger 13 about its longitudinal axis will also rotate the head 18 and break it loose from the barrel 11 at the weakened groove 21.

Figure 2:
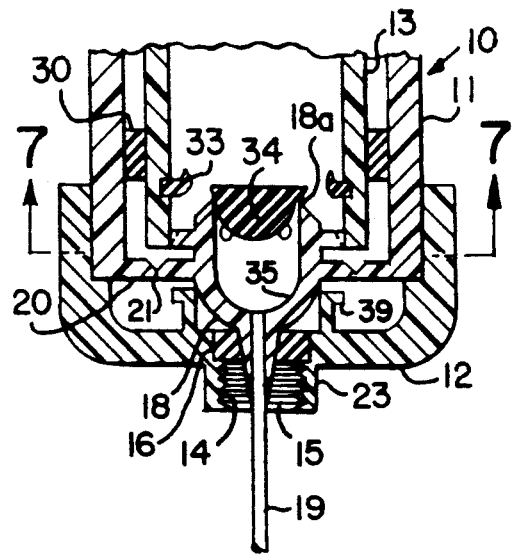
FIG. 2 is a fragmentary side elevational view of the front end of the syringe shown in FIG. 1 with portions broken away to show the plunger depressed to break the covering on the front end of the hollow plunger.
Figure 3:
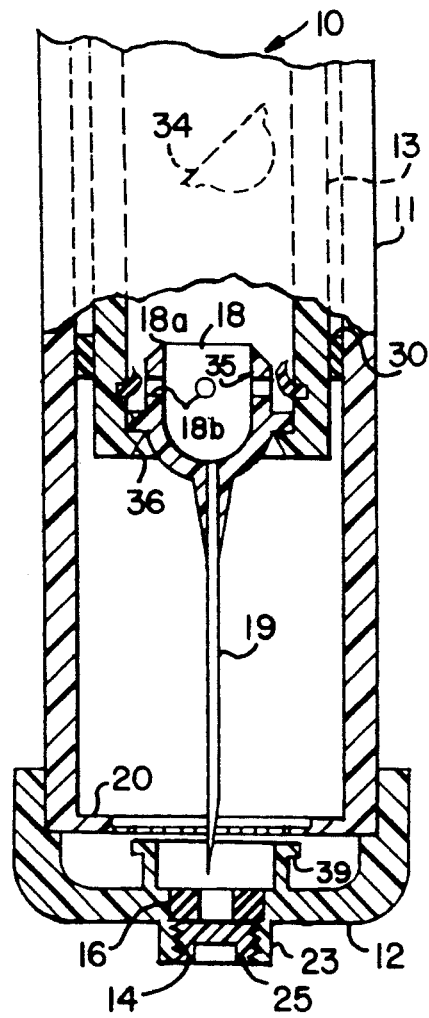
FIG. 3 is a fragmentary side elevational view of the syringe shown in FIG. 1 with portions broken away to show the plunger and needle retracted into the barrel.

In giving an injection, the syringe 10 is first filled with medication fluid by removing the sheath 24 from the needle 19, inserting the needle into a container of fluid and pulling the plunger 13 rearwardly in the barrel 11. The needle 19 is then inserted in the patient to be treated and the plunger is depressed a sufficient distance into the barrel 11 to expel the medication fluid from the barrel. The needle 19 is withdrawn from the patient and the plunger 13 is depressed further to rupture and break loose the cover 33 from the end of the barrel as shown in FIG. 2. by contact of a cutting edge 18a on the head 18 against the cover 33. The head 18 also contains drain holes 18b to aid in expelling the fluid from the barrel 11. The plunger 13 is then rotated about its longitudinal axis to bring the slots 37 into alignment with the pegs 38. Once the pegs 38 are engaged in interlocking relationship with the slots 37, the plunger 13 is again rotated about its longitudinal axis to cause the head 18 to rotate and to break loose from the barrel 13 at the weakened groove 21 as previously mentioned. The plunger 13 is then depressed a further distance sufficient for the rib 36 to engage the portion of the connector wall 20 which remains attached to the head 18 and to withdraw the head 18 and the needle 19 into the barrel as shown in FIG. 3. The plug 25 is then screwed into the center hole 14 to prevent the needle 19 from coming out of the barrel 11.

The plunger 13 is again depressed fully toward the front of the barrel 11 until the rib 36 engages a radially outwardly extending annular rib 39 on the front end cap 12 and locks the plunger 13 inside the barrel 11 to prevent removal of the plunger and the needle 19. Thus the needle 19 is retained in the barrel in such manner that it will not project out the front of the barrel 11 and cannot be removed from the rear of the barrel without destroying the syringe 10 and rendering it useless. In order to prevent compression resistance to the plunger 13 being depressed so that it encloses the needle head 18 and needle 19 in the chamber 32 the chamber is vented at its rear end by vent holes 40 which permit any internal pressure to be released into the atmosphere or into the portion of the barrel to the rear of the seals 30.

Figure 8:
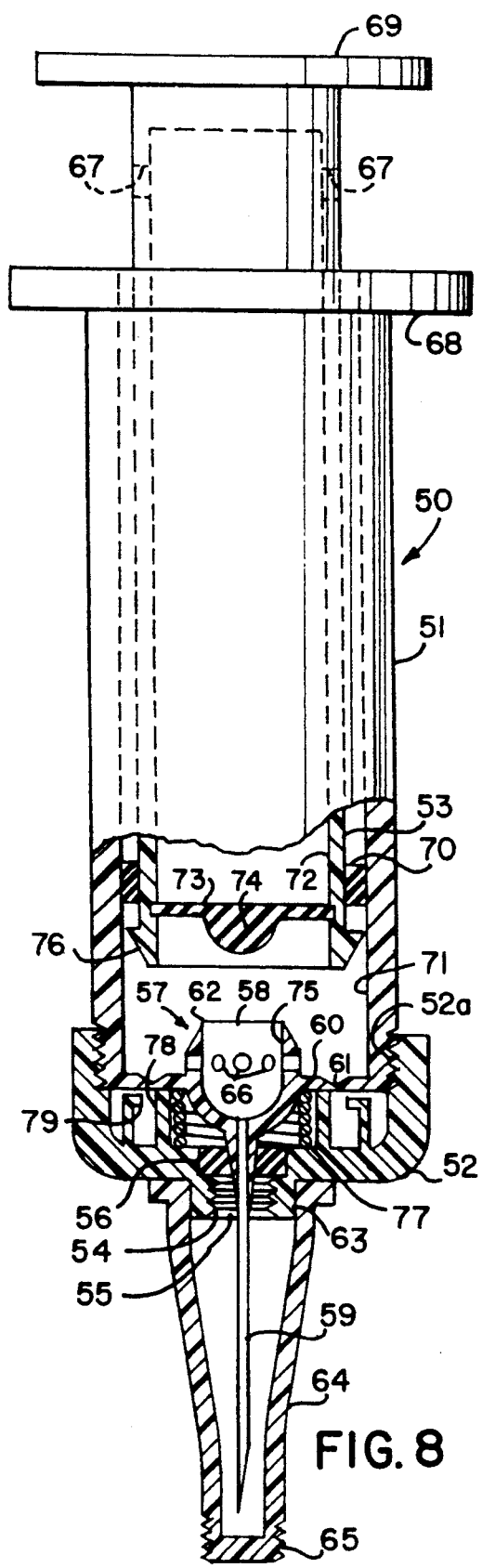
FIG. 8 is side elevational view of a syringe illustrating another embodiment of the invention with portions broken away to show the internal mechanism of the device which includes a compression spring.
Figure 9:
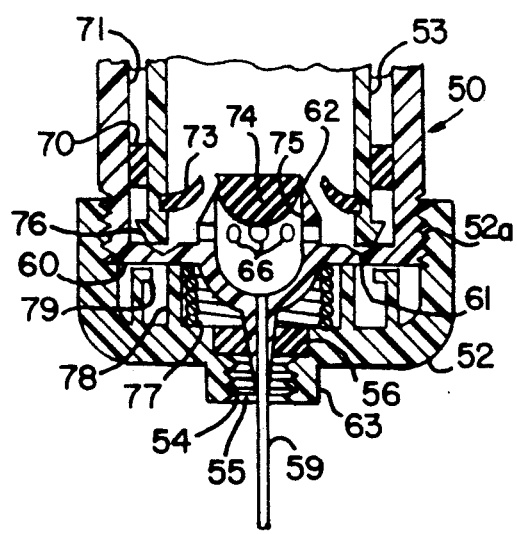
FIG. 9 is a fragmentary side elevational view of the embodiment shown in FIG. 8 with the plunger depressed to break the end cover on the hollow plunger.
Figure 10:
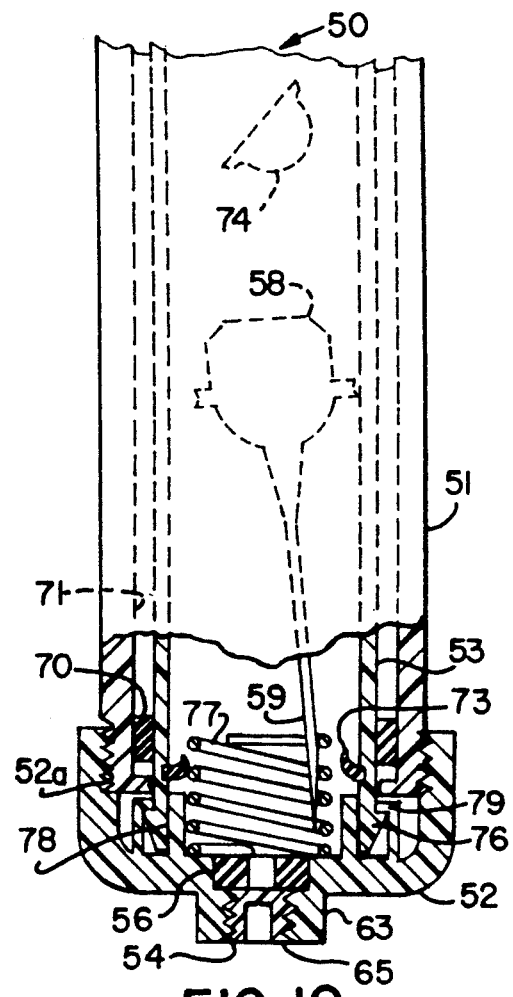
FIG. 10 is a fragmentary side elevational view of the embodiment shown in FIG. 8 with the plunger depressed even farther to break loose the needle retainer and with the needle propelled into the hollow plunger and the plunger locked in the depressed position within the barrel.

While the cap 12 is described as being adhesively secured to the barrel 11, it can also be secured to the barrel by other means such as heat sealing or it can be screwed on by using a threaded coupling as shown in the embodiment shown in FIGS. 8 through 10.

Referring now to FIGS. 8 through 10, this embodiment is similar in some respects to the embodiment previously described in FIGS. 1 through 7 except that instead of using manual retraction of the needle, it uses a spring retracted needle.

In the embodiment in FIGS. 8 through 10, a hypodermic syringe is indicated generally by the numeral 50. The syringe 50 has a hollow cylindrical barrel 51 which is open at the rear end and covered at the front end by a front end cap 52 which is secured by a threaded joint 52a or by other suitable means to the barrel 51. The end cap 52 has a center hole 54, part of which has internal threads 55 and the remainder carries an elastomeric seal ring 56.

Attached to the front end of the barrel 51 is a needle assembly 57 which includes a head member 58 containing a needle 59 molded therein and a radially outwardly extending annular connector wall 60 extending between the barrel 51 and the needle head member 58 to temporarily secure the needle in the end of the barrel 51 with the needle 59 projecting out through the center hole 54 and sealing with the ring 56 to prevent fluid from leaking from the barrel 51 around the outside of the needle 59. The connector wall has an annular groove 61 to serve as a weakened portion to permit the needle head 58 to be broken away from the barrel 51 as will be explained later. The groove 61 may contain a plurality of spaced apart holes similar to the holes 22 shown in FIG. 6, to further weaken the area of the groove 61 to permit break-away of the needle head 58 as will be explained later. The head 58 also has drain holes 66 to aid in expelling fluid from the barrel 51 when an injection is given.

The cap 52 has an outwardly projecting shoulder portion 63 in axial alignment with the center hole 54 for receiving a sheath 64 which covers the needle 59 until it is removed to give an injection. The sheath 64 has a break-away threaded plug 65 at the front end thereof which is screwed into the threaded portion of the center hole 54 to retain the needle 59 inside the barrel 51 after it has been retracted.

The modified type of snap in plug 25a shown in FIG. 4A can also be substituted for the screw-in threaded plug 65 in this embodiment of the invention.

The barrel 51 has a radially outwardly extending flange 68 at the rear end thereof to aid in holding the barrel 51 while depressing the plunger 53 by pressing on an enlarged end plate 69 on the rear end of the plunger 53.

The plunger 53 fits inside the barrel 51 and is moveable axially backward and forward within the barrel. An annular seal ring 70 surrounds the plunger 53 near the front end thereof and provides a seal with the inner wall surface 71 of the barrel 51 to retain injection fluid and pressure within the barrel 51. The plunger 53 has a hollow chamber 72 which is sealed from the interior of the barrel 51 by a resilient rupturable cover 73 made preferably of elastomeric material. The cover has a hemispherical portion 74 which extends forwardly into a hollow cup shaped cavity 75 in the needle head 58 to aid in expelling fluid from the cavity when the plunger 53 is depressed.

At the front end of the plunger 53, an annular rib or ledge 76 extends radially outwardly for performing a function to be described later.

In giving an injection with the embodiment shown in FIGS. 8 through 10, the same procedures are followed as previously described for the embodiment shown in FIGS. 1 through 7 up to the step of withdrawing the needle from the patient. The plunger 53 is then depressed further to rupture and break loose the cover 73 from the end of the barrel 51 by contact of a sharp edge 62 on the head 58 against the cover 73 as shown in FIG. 9. The plunger 53 is then depressed a further distance sufficient for the front end of the barrel 51 to engage the weakened portion 61 of the connector wall 60 and break loose the head 58 from the barrel 51.

Once the head 58 is broken loose, a spring 77 contained within an annular wall 78 expands and propels the head 58 and needle 59 into the hollow chamber 72 in the plunger as shown in FIG. 10. Vent holes 67 are provided at the rear end of the plunger 53 to vent the hollow chamber 72 so that the needle head 58 will not meet compression resistant when it is propelled into the chamber.

The plug 65 is then screwed into the center hole 54 to prevent the needle 59 from coming out of the barrel 51. The plug 65 on the sheath 64 is screwed into the hole 54, then the sheath 64 can be broken off leaving the plug 65 in the hole.

The plunger 53 is depressed fully toward the front of the barrel 51 until the rib 76 engages a radially inwardly extending annular rib 79 on the front end cap 52 and locks the plunger 53 inside the barrel 51 to prevent removal of the plunger 53 and the needle 59 in the same manner that the needle was locked into the barrel 11 in the embodiment of FIGS. 1 through 7.

The barrels, plungers and other main components of the embodiments shown herein are made preferably of plastics which can be made by injection molding or other suitable manufacturing methods. While the needle assemblies 17 and 57 are shown molded as an integral part of the barrels 31 and 51 respectively, it should be recognized that they may be made as separate parts and attached to the barrel in any suitable manner. It should also be recognized that the detailed contours and proportions of the various components can vary from some of the illustrations shown in the drawings without departing from the scope of the invention. These and various other modifications can be made in the embodiments shown and described herein without departing from the scope of the invention.

I claim:

1. A safety hypodermic syringe comprising:
   (A) a hollow barrel for containing a fluid, having a rear end opening and a front end opening;
   (B) a hollow needle extending through the front end opening of the barrel to permit fluid from the barrel to be injected through the needle;
   (C) mounting means temporarily securing the needle within the front end of the barrel with the needle protruding forwardly from the front end opening of the barrel until an injection given by the needle has been completed;
   (D) a hollow plunger containing an axial chamber therein which is large enough to receive the needle and mounting means therein, the plunger having a front end inserted through the rear end opening of the barrel and being slideable longitudinally within said barrel to move inwardly when pressure is applied to an outwardly extending rear end of the plunger, the front end of the plunger being open for communication between the axial chamber and the interior of the barrel except when the end is initially covered by an end cover which temporarily seals the chamber of the plunger until the plunger is depressed a sufficient distance to complete the injection of fluid from the chamber through the needle;
   (E) means removing the end cover from the front end of the plunger;
   (F) means moving the needle rearwardly out of the front end opening of the barrel with at least part of the mounting means and into a stored position within the hollow plunger; and
   (G) means to retain the needle and mounting means in the stored position to prevent the needle from protruding from the front end of the barrel.

2. The safety hypodermic syringe as claimed in claim 1 wherein the needle has a head member attached to one end which is secured to the interior of the barrel at the front thereof, said head member having a sharpened edge portion for cutting open the end cover of the plunger when the plunger is fully depressed to permit the needle and the head member and to be moved out of the front end opening of the barrel and into a stored position in the axial chamber of the plunger.

3. The safety hypodermic syringe as claimed in claim 2 wherein the means moving the needle and mounting means from the front end opening and into a stored position is an interlocking means for temporarily locking together the plunger and the head member to permit the head member to be rotated by manual rotation of the plunger to cause the head member to break loose from the barrel and wherein the means moving the needle and mounting means into a stored position further includes a radially inwardly extending rib means at the front end of the plunger which engages a radially outwardly extending rib means on the head member after the head member has been broken loose from the barrel and permits the needle and head member to be withdrawn from the front end opening and into the barrel by partially withdrawing the plunger from the barrel.

4. The safety hypodermic syringe as claimed in claim 1 wherein the means to retain the needle in the stored position is a plug which is inserted in the front end opening of the barrel after the needle has been withdrawn therefrom.

5. The safety hypodermic syringe as claimed in claim 4 wherein the front end opening of the barrel is a threaded hole and the plug contains threads which match the threads of the hole.

6. The safety hypodermic syringe as claimed in claim 4 wherein the plug is a snap-in type device having a yieldable portion which flexes to permit insertion in the front end opening of the barrel but which expands after insertion to retain the plug in the opening.

7. The safety hypodermic syringe as claimed in claim 3 including a sheath member covering the portion of the needle which projects from the front end opening of the barrel and wherein the plug for closing the front end opening after withdrawal of the needle into the barrel is a breakaway portion on one end of the sheath which covers the needle.

8. The safety hypodermic syringe as claimed in claim 1 including means to vent the chamber of the hollow plunger to prevent a buildup of pressure within the cavity which might resist movement of the needle and mounting means into the chamber.

9. The safety hypodermic syringe as claimed in claim 2 wherein the means moving the needle and mounting means from the front end opening and into a stored position is a frangible connector means extending radially outwardly from the head member and attached to a wall surface on the interior of the barrel near the front end thereof and a compressed spring bearing against the connector means to bias the head member toward the rear end of the barrel and the plunger and causing the needle and head member to be propelled into the cavity of the plunger when the plunger is fully depressed and when the end of the plunger breaks the frangible connector.

10. The safety hypodermic syringe as claimed in claim 9 wherein the means to retain the needle in the stored position is a plug which is inserted in the front end opening of the barrel after the needle has been withdrawn therefrom.

11. The safety hypodermic syringe as claimed in claim 10 wherein the front end opening of the barrel is a threaded hole and the plug contains threads which match the threads of the hole.

12. The safety hypodermic syringe as claimed in claim 9 including a sheath member covering the portion of the needle which projects from the front end opening of the barrel and wherein the plug for closing the front end opening after withdrawal of the needle into the barrel is a breakaway portion on one end of the sheath which covers the needle.

13. The safety hypodermic syringe as claimed in claim 9 including means to vent the chamber of the hollow plunger to prevent a buildup of pressure within the cavity which might resist movement of the needle and mounting means into the chamber.

14. A safety hypodermic syringe as claimed in claim 1 wherein the front end of the barrel includes an end cap secured thereto.

15. A safety hypodermic syringe as claimed in claim 14 wherein the end cap is adhesively secured to the barrel.

16. A safety hypodermic syringe as claimed in claim 14 wherein the end cap is secured on the barrel by a threaded joint.

17. A safety hypodermic syringe comprising:
(A) a hollow barrel for containing a fluid, having a rear end opening and a front end opening of smaller diameter than the rear end opening;
(B) a needle assembly having a hollow needle with a front and rear end and a head portion attached to the needle at the rear end thereof;
(C) separable means temporarily mounting the needle assembly in the front end of the barrel with the front end of the needle protruding forwardly through the front end opening of the barrel in a ready position for injection of fluid from the barrel and the rear end of the needle and the head portion extending into the barrel at the front end thereof, said hollow needle providing communication between the inside and outside of the barrel;
(D) a hollow plunger containing an axial chamber therein which is large enough to receive the needle assembly therein and having a front end thereof inserted through the rear end opening of the barrel and being longitudinally slideable within said barrel to move inwardly when pressure is applied to an outwardly extending rear end of the plunger, the front end of the plunger being open for communication with the interior of the barrel except when the end is initially covered by a removeable end cover which temporarily seals the chamber of the plunger until the plunger is depressed a sufficient distance to inject fluid from the chamber through the needle;
(E) means removing the end cover from the front end of the plunger;
(F) means withdrawing the needle assembly and separable means from sealing engagement with the front end opening of the barrel and moving the needle assembly and yieldable means into the barrel and into a retracted position within the axial chamber of the plunger;
(G) means closing the front end opening of the barrel after withdrawal of the needle assembly into the barrel to prevent the needle from protruding from the front of the barrel; and
(H) means locking the plunger in the depressed position within the barrel after the needle assembly has been stored in the chamber of the plunger.

18. The safety hypodermic syringe as claimed in claim 17 wherein the head portion of the needle assembly is a cup shaped member positioned within the interior of the barrel at the front thereof, said head portion having a sharpened edge portion for cutting open the end cover of the plunger when the plunger is fully depressed to permit the needle assembly and the yieldable means to be moved out of the front end opening of the barrel and into a stored position in the axial chamber of the plunger.

19. The safety hypodermic syringe as claimed in claim 18 wherein the means withdrawing the needle assembly and the separable means from the front end opening and moving them into a stored position is an interlocking means for temporarily locking together the plunger and the head member to permit manual rotation of the plunger and head member to break the head member loose from the barrel and wherein the means withdrawing the needle assembly further includes a radially inwardly extending rib member at the front end of the plunger which engages a radially outwardly extending rib member on the head portion after the head portion has been broken loose from the barrel and permits the needle and head portion to be withdrawn from the front end opening and into the barrel by partially withdrawing the plunger from the barrel.

20. The safety hypodermic syringe as claimed in claim 17 wherein the means to retain the needle assembly in the stored position is a plug which is inserted in the front end opening of the barrel after the needle assembly has been withdrawn therefrom.

21. The safety hypodermic syringe as claimed in claim 20 wherein the front end opening of the barrel is a threaded hole and the plug contains matching threads.

22. The safety hypodermic syringe as claimed in claim 20 wherein the plug is a snap-in type device having a yieldable portion which flexes to permit insertion in the front end opening of the barrel but which expands after insertion to retain the plug in the opening.

23. The safety hypodermic syringe as claimed in claim 20 including a sheath member covering the portion of the needle which projects from the front end opening of the barrel and wherein the plug for closing the front end opening after withdrawal of the needle into the barrel is a breakaway portion on one end of the sheath which covers the needle.

24. The safety hypodermic syringe as claimed in claim 17 including means to vent the chamber of the hollow plunger to prevent a buildup of pressure within the cavity which might resist movement of the needle assembly into the chamber.

25. The safety hypodermic syringe as claimed in claim 18 wherein the means withdrawing the needle assembly and the yieldable means from the front end opening and moving them into a stored position is a frangible connector means extending radially outwardly from the head member and attached to a wall surface on the interior of the barrel near the front end thereof and a compressed spring bearing against the connector means to bias the head member toward the rear end of the barrel and the plunger and causing the needle and head member to be propelled into the cavity of the plunger when the plunger is fully depressed and when the end of the plunger breaks the frangible connector.

26. A safety hypodermic syringe as claimed in claim 17 wherein the front end of the barrel includes an end cap secured thereto.

27. A safety hypodermic syringe as claimed in claim 26 wherein the end cap is adhesively secured to the barrel.

28. A safety hypodermic syringe as claimed in claim 26 wherein the end cap is secured on the barrel by a threaded portion which engages a threaded portion on the barrel.

29. A safety hypodermic syringe comprising:
(A) a hollow barrel for containing a fluid, having a rear end opening and a separable needle mounting means integral with the front end thereof for temporarily securing a hollow needle within the front end of the barrel with the needle protruding forwardly from the front end of the barrel until an injection given by the needle has been completed;
(B) a hollow plunger containing an axial chamber therein which is large enough to receive the needle and mounting means therein, the plunger having a front end inserted through the rear end opening of the barrel and being slideable longitudinally within said barrel to move inwardly when pressure is applied to an outwardly extending rear end of the plunger, the front end of the plunger being open for communication between the axial chamber and the interior of the barrel except when the end is initially covered by an end cover which temporarily seals the chamber of the plunger until the plunger is depressed a sufficient distance to complete the injection of fluid from the chamber through the needle;
(C) a front end closure cap secured to the front end of the barrel enclosing the needle mounting means and having a central opening therein through which the needle projects forwardly therefrom;
(D) means removing the end cover from the front end of the plunger;
(E) means separating the needle mounting means from the front end of the barrel;
(F) means moving the needle rearwardly from the front end of the barrel with at least part of the mounting means and into a stored position within the hollow plunger; and
(G) means to retain the needle and mounting means in the stored position to prevent the needle from protruding from the front of the barrel.

* * * * *